(12) United States Patent
Raghuraman et al.

(10) Patent No.: US 8,241,393 B2
(45) Date of Patent: *Aug. 14, 2012

(54) METHODS AND ARTICLES FOR GOLD NANOPARTICLE PRODUCTION

(75) Inventors: Kannan Raghuraman, Columbia, MO (US); Kattesh K. Katti, Columbia, MO (US); Kavita K. Katti, Columbia, MO (US); Henry W. White, Columbia, MO (US); Cathy S. Cutler, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 1343 days.

This patent is subject to a terminal disclaimer.

(21) Appl. No.: 11/219,497

(22) Filed: Sep. 2, 2005

(65) Prior Publication Data

US 2007/0051202 A1    Mar. 8, 2007

(51) Int. Cl.
B22F 9/24 (2006.01)
(52) U.S. Cl. .......................................................... 75/370
(58) Field of Classification Search ..................... 75/370
See application file for complete search history.

(56) References Cited

U.S. PATENT DOCUMENTS

| | | | |
|---|---|---|---|
| 3,717,701 A | | 2/1973 | Carlson |
| 3,847,279 A * | | 11/1974 | Montgomery ................ 206/219 |
| 5,541,289 A * | | 7/1996 | Gilbertson ................... 530/327 |
| 5,948,386 A | | 9/1999 | Katti et al. |
| 6,103,868 A | | 8/2000 | Heath et al. |
| 6,572,673 B2 | | 6/2003 | Lee et al. |
| 6,818,199 B1 | | 11/2004 | Hainfeld et al. |
| 2005/0054613 A1 | | 3/2005 | Katti et al. ..................... 514/80 |
| 2006/0045916 A1 | | 3/2006 | Raghuraman et al. ......... 424/489 |

FOREIGN PATENT DOCUMENTS

WO   WO 03/072053   *   9/2003
WO   WO 03/072053 A2   9/2003

OTHER PUBLICATIONS

Bhargava, S.K. et al, Langmuir, 2005, 21(13), 5949-5956.*
Weare, W.W. et al, J.Am. Chem.Soc. 2000, 122(51), 12890-12891.*
Daniel, M.C. Chem. Rev., 2004, 104, 293-346.*
Balogh, L.P., et al, Pharma Chem 2003, 2(4), 94-98.*
Shao, Y. et al, Chem. Comm. 2004, 1104-1105.*
Metzler, Biochemistry, 1977, pp. 88-90.*
"Synthesis and Characterization of Stable Aqueous Dispersion of Silver Nanoparticles Through the Tollens Process," Yin et al., J. Mater. Chem., 12, 522-527 (2002).
"Green Technique Makes Silver Nanoparticles," L. Kalaugher, Nanotechweb.org., (Jan. 2004).
"Reduction of Silver Nanoparticles in DMF. Formation of Monolayers and Stable Colloids," I. Pastoriza-Santos et al., Pure Appl. Chem., vol. 72, Nos. 1-2, pp. 83-90 (2000).
"Superlattices of Silver Nanoparticles Passivated by Mercaptan," S. He et al., Journal of Physics D: Applied Physics 34, 3425-3429 (2001).
"Characterization of Supramolecular $(H_2O)_{18}$ Water Morphology and Water-Methanol $(H_2O)_{15}(CH_3OH)_3$ Clusters in a Novel Prosperous Functionalized Trimeric Amino Acid Host," K. Raghuraman et al., J. Am. Chem. Soc., 125 (23) pp. 6955-6961 (2003).
Jorge Gardea-Torresdey, "Plants with Midas Touch: Formation of Gold Nanoparticles by Alfalfa Plants," University of Texas at El Paso. Believed published circa 2002 on the World Wide Web at: http://www-ssrl.slac.stanford.edu/research/highlights_archive/alfalfa.html.
Beomseok Kim et al., "Tuning the Optical Properties of Large Gold Nanoparticle Arrays," Mat. Res. Soc. Symp. Proc. vol. 676, Materials Research Society (2001).
Beomseok Kim et al., "Self-Organization of Large Gold Nanoparticle Arrays," J. Am. Chem. Soc., 123, 7955-7956 (2001).
Santanu Bhattacharya et al. "Synthesis of gold nanoparticles stabilised by metal-chelator and the controlled formation of close-packed aggregates by them," Proc. Indian Acad. Sci. (Chem. Sci), vol. 115, Nos. 5 & 6. pp. 613-619, (Oct.-Dec. 2003).
Volkert, W.A., T.J. Hoffman, "Therapeutic Radiopharmaceuticals," Chem. Rev. (Review) 99 (9); 2269-2292, 1999.
Balogh, Lajos P. Shraddha S. Nigavekar, Andrew C. Cook, Leah Minc, Khan, Mohamed K., "Development of dendrimer-gold radioactive nanocomposites to treat cancer microvasculature," PharmaChem 2(4): 94-44, 2003.
Kandikere Ramaiah Prabhu et al. "De novo synthetic design for air-stable *bis* primary phosphines: Synthetic, catalytic and biomedical motifs," Special Section: Non-Metal Chemistry; Current Science, vol. 78, No. 4, Feb. 25, 2000.
P. Raveendran, et al., "Completely "Green" Synthesis and Stabilization of Metal Nanoparticles," Journal of the American Chemical Society, Oct. 22, 2003, 125(46), pp. 13940-13941.
Office Action mailed Apr. 15, 2009 in U.S. Appl. No. 10/931,174.
Neil G. Connely "Nomenclature of Inorganic Chemistry IUPAC Recommendations 2005," International Union of Pure and Applied Chemistry, 2005, p. 51-52.
Office Action mailed Feb. 3, 2010 in U.S. Appl. No. 10/931,174.

* cited by examiner

*Primary Examiner* — Shaojia Anna Jiang
*Assistant Examiner* — Ganapathy Krishnan
(74) *Attorney, Agent, or Firm* — Greer Burns & Crain Ltd.

(57) ABSTRACT

An example embodiment of a method for making gold nanoparticles includes steps of reacting a gold salt with a phosphino amino acid. Example phosphino amino acids include trimers, with a particular example being a trimeric amino acid conjugate containing one phosphino group. In an example method of the invention, the gold nanoparticles may be produced in timer periods of less than about 3 minutes, and at temperatures of less than about 30° C. Other methods of the invention are directed to methods for stabilizing gold nanoparticles, and to methods for making gold nanochains.

23 Claims, 1 Drawing Sheet

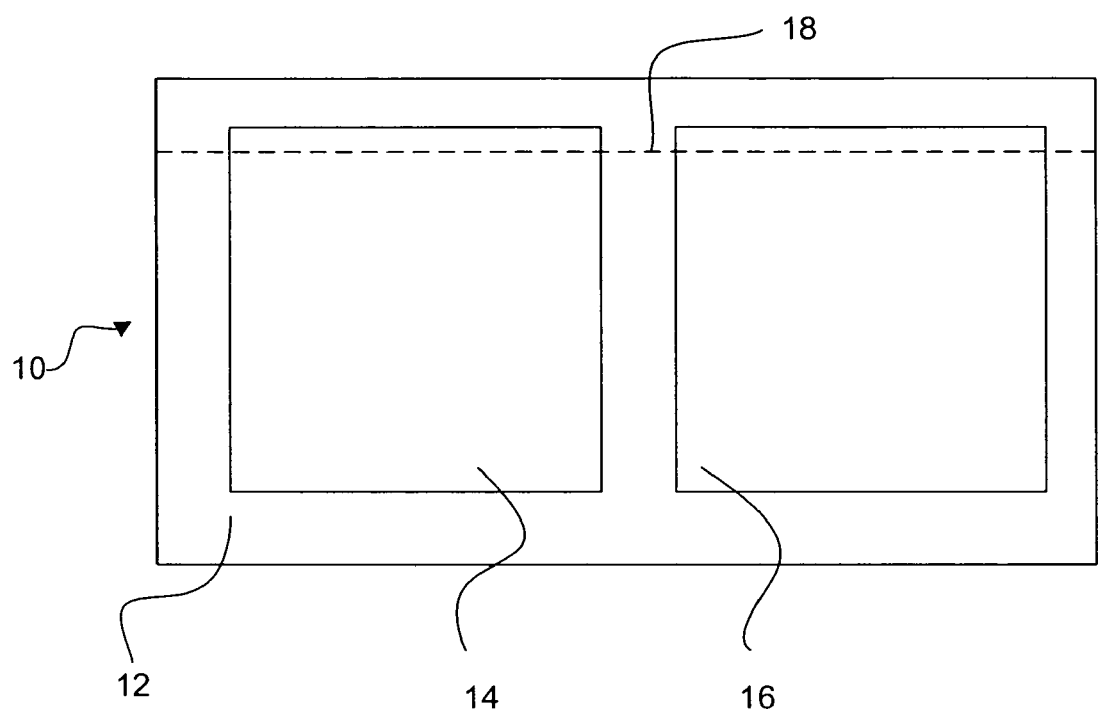

METHODS AND ARTICLES FOR GOLD NANOPARTICLE PRODUCTION

STATEMENT OF GOVERNMENT INTEREST

This invention was made with government support under Grant Nos. 5RO1CA1 19412-01 and Grant No. 1R21CA128460-01 awarded by the National Institutes of Health (NIH). The government has certain rights in the invention.

FIELD OF THE INVENTION

A field of the invention is methods for producing gold nanoparticles, including nanochains. Another field of the invention is methods for stabilizing gold nanoparticles, including gold nanochains.

BACKGROUND

Gold nanoparticles have a multitude of valuable applications as catalysts, in semiconductors, in the rapidly emerging fields of nanoscience and nanotechnology, medical imaging, biomedicine, therapeutics and others. Powerful surface plasmon absorption of gold, for example, makes gold nanoparticles useful in applications such as biosensors. They are environmentally and biologically benign. Other example gold nanoparticle applications include smart windows, rewritable electronic paper, electronic panel displays, memory components, and others.

Many traditional methods for the production of gold nanoparticles require use of potentially harmful chemicals such as hydrazine, sodium borohydride and dimethyl formamide ("DMF") in lengthy synthetic processes. These chemicals pose handling, storage, and transportation risks that add substantial cost and difficulty to gold nanoparticle production. These harmful chemicals also make it impractical, if not impossible, to produce gold nanoparticles in-vivo. Some production methods include the application of sodium borohydride to reduce a gold salt to produce gold nanoparticles. This production method is unsuitable in the presence of target specific peptides because sodium borohydride will reduce chemical functionalities present on peptide backbones, thus either reducing or eliminating the biospecificity of biomolecules. Still another disadvantage of many methods for producing gold nanoparticles relates to the heat required for their production. This adds further costs and complications to production of gold nanoparticles.

Still other problems in the art relate to production of gold nanoparticle chains and arrays. Many applications benefit from the use of nanochains verses nanoparticles. In some imaging applications, for example, individual nanoparticles may not be detectable. A nanochain or nanoarray, on the other hand, is more easily detected. In the prior art predictable and consistent methods for producing gold nanochains and arrays are not known.

Still other problems relate to the relatively instability of nanoparticles. Gold nanoparticles tend to quickly agglomerate and/or to oxidize. Known stabilization methods include storage in citrate. Citrates can be strongly acidic, making their handling and use difficult. Also, transfer of the gold nanoparticle from the stabilizing citrate is also difficult. For materials such as nitrates, glucoses, starches, and nitrogen-based materials, for example, transfer of gold nanoparticles from a citrate stabilizer is very difficult or even impossible. The sodium borohydride reduction method typically uses thiols to stabilize gold nanoparticles. Gold nanoparticles stabilized by thiols cannot be readily exchanged onto peptides or other biomolecules because of the strong interaction of gold metal with thiol groups.

Still other problems are related to obtaining a desired size of gold nanoparticles. Currently known production methods do not allow for well defined size distribution of gold nanoparticles.

Other problems in the art relate to radioactive gold nanoparticles. Radioactive gold nanoparticles are useful, for example, in nanomedicine applications. Gold nanoparticles are potentially useful for treatment of disease as they can deliver agents directly into cancerous cells and cellular components (e.g., a tumor site) with a higher concentration of radioactivity (higher dose of radioactivity). Each gold nanoparticle contains several atoms of gold, which are typically radioactive Au-198/199. Radioactive gold nanoparticles can also be easily tagged with oligonucleotides and peptides that are selective for receptors over expressed by diseased tissue. These unique advantages present promising opportunities in the design and development of tumor specific nanotherapeutic agents for the treatment of cancer. Unfortunately, traditional production methods for gold nanoparticles have proven to be problematic when using radioactive gold. By way of example, traditional methods that utilize $NaBH_4$ (or other reducing agents) for the production of gold nanoparticles at macroscopic levels often fail when used at tracer levels to produce nanoparticulate radioactive Au-198/199.

SUMMARY

One example embodiment of a method for making gold nanoparticles includes steps of providing a gold containing material, providing a phosphino amino acid, and reacting the gold salt with the phosphino amino acid to make gold nanoparticles. Example phosphino amino acids include trimers, with a particular example being a trimeric amino acid conjugate containing one phosphino group. Example gold containing materials include gold salts. An additional embodiment of the invention is an article with a plurality of sealed compartments, one each of said compartments containing a gold containing material and a phosphino amino acid.

BRIEF DESCRIPTION OF THE DRAWINGS

FIG. 1 is a schematic of an article of the invention.

DESCRIPTION OF EXAMPLE EMBODIMENTS

Examples of methods of the present invention include methods for making gold nanoparticles. Some methods of the invention generally include the steps of reacting a gold containing material, which is preferable a gold salt such as $NaAuCl_2 xH_2O$ or $NaAuCl_4$, with a phosphino amino acid. Methods of the invention have been discovered to offer numerous and valuable advantages over the prior art. For example, the gold salt and phosphino amino acid reactants are environmentally and biologically benign materials that do not require special handling or storage. Reactions of the invention may be carried out at or near physiological pH. Methods of the invention are therefore useful for in-vivo gold nanoparticle production. Gold nanoparticles may be produced through methods of the invention at relatively high conversions at ambient temperature. Accordingly, a one-pot environmentally and biologically benign synthesis method for gold nanoparticles at ambient temperature is provided. These and other advantages will be(apparent to those skilled in the art when considering the detailed description of example methods of the invention that follow.

One example method of the invention includes reacting a gold salt with a phosphino amino acid, with one particular example method including the steps of performing the reaction:

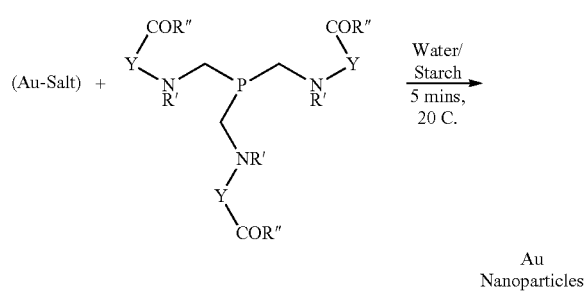

where:
X=OH, Cl, Br, I or $NO_3$
R'=Hydrogen, alkyl ($C_1$-$C_6$), or amino protecting group
R''=$OR^A$, $NR^A R^B$ or $R^C$; where $R^A$=$R^B$=hydrogen, alkyl, phenyl, benzyl, or a carboxyl protecting group; or $R^A$=$R^B$=pyrollidino, piperdino, or thiomorpholinno ring; and $R^C$=alkyl, phenyl or benzyl
Y=Residue of an amino acid.

Although a trimer amino acid is illustrated and is preferred, a dimer, polymer, or a monomer is also believed to be suitable for use.

The phosphino amino acid is preferably a conjugate amino acid. A preferred phosphino amino acid is a trimeric alanine phosphine conjugate ("TAAC" or $P(CH_2NHCH_3COOH)_3$) which upon interaction with $NaAuCl_4$ in water at 25° C. at physiological pH produces gold nanoparticles in excellent yield and number density. TAAC has the structure:

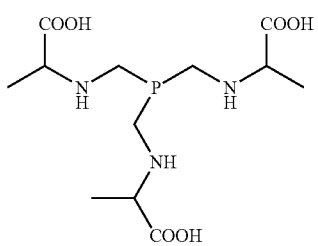

TAAC is described in WIPO International Application No. PCT/US03/05678, Publication No. WO 03/072053, "Compounds for treatment of copper overload," by Katti, Kavita K.; Kannan, Raghuraman; Casteel, Stan W.; Katti, Kattesh V; as well as in "Characterization of Supramolecular $(H_2O)_{18}$ Water Morphology and Water-Methanol $(H_2O)_{15}(CH_3OH)_3$ Clusters in a Novel Phosphorus Functionalized Trimeric Amino Acid Host," by Raghuraman, K.; Katti, K. K.; Barbour, L. J.; Pillarsetty, N.; Barnes, C. L.; Katti, K. V.; *J. Am. Chem. Soc.;* 2003; 125(23); 6955-6961; each of which are incorporated by reference herein for purposes of further illustrating the field and background of the invention. Phosphino amino acids useful in methods of the invention, with TAAC being one example, are environmentally and biologically benign compounds that are stable and easily handled. As such, their use offers substantial advantages over methods of the prior art that require hazardous, biologically/environmentally unfriendly reactants that are more difficult and costly to store and handle.

Example methods for making gold nanoparticles are as follows:

EXAMPLE PROCEDURE #1 (PERFORMED AT 25° C.)

0.1875 gm of starch was added to 50 ml DI water and heated to about 100° C. to dissolve the starch
In a separate container, 0.0337 gm of TAAC was dissolved in 1 ml DI water.
A stock solution of gold was prepared by dissolving 0.039 gm of $NaAuCl_4$ in 1 ml of DI water.
In a separate 20 ml vial, 6 ml of the starch solution was combined with 100 µl of the $NaAuCl_4$ solution with stirring.
20 µl of the TAAC solution was added to the 20 ml vial containing the starch/gold solution, with stirring.

Color changes to yellow-brown substantially instantaneously, indicating conversion of the gold in the gold salt to gold nanoparticles. Stirring was continued for about 30 minutes to ensure complete conversion. The gold nanoparticles produced through this example method were stored in DI water for over 7 days without agglomeration.

EXAMPLE PROCEDURE #2 (PERFORMED AT 25° C.)

For some biomedical applications of gold nanoparticles, including their use in X-ray contrast enhancers and also in X-ray based therapy, it is important to produce and stabilize gold nanoparticles in biocompatible formulations. Biocompatible formulations include development of synthetic processes that allow synthesis without the use of harsh chemicals. The following process allows the use of water as the solvent and also biocompatible phosphate buffer and edible gum Arabic as nanoparticle initiates and stabilizers:

Gum Arabic (GA) solution is prepared by dissolving 12 mg in 6 ml of phosphate buffer concentrate (7 pH).
To the reflux solution of GA solution, 0.1 ml of 0.1 M $NaAuCl_4$ is added with continuous stirring.
The color of the solution changes immediately from clear to dark red indicating the formation of gold nanoparticles.
Stirring is continued for 2 minutes.

Final confirmation of the formation of gold nanoparticles was obtained from UV spectroscopy which showed plasmon resonance and also through electron microscopy which showed uniformly sized gold nanoparticles in the 15-30 nm size range. The gold nanoparticles as produced above are stable in water at physiological pH for over six months. These nanoparticles are well suited for biomedical applications including, CT (computer tomography) X-ray imaging, ultrasound imaging, X-ray therapy, through, for example, injecting nanoparticles in aqueous media intravenously (IV).

Reactions of the invention for the formation of gold nanoparticles are quantitative. For economic and other reasons, an excess of phosphino amino acid is preferably provided to ensure complete conversion of the relatively costly gold salt. The reaction preferably proceeds with at least about 98% conversion—at least about 98% of the gold in the gold salt is converted to gold nanoparticles. There are substantially no byproducts—the phosphino amino acid is oxidized during the reaction to yield a corresponding oxide, which is further consumed for assisting the conversion of the gold salt to gold nanoparticles. The reduction of the gold salt is initiated by phosphine. The phosphine in turn is oxidized to phosphine oxide (e.g., TAAC oxide). After these initial steps, the aminocarboxylates in the phosphine oxide serve as a reducing agent to reduce gold salt to gold nanoparticles. To aid the reaction, it is preferred that a solvent such as water is provided, along with a stabilizer such as starch.

The reaction proceeds substantially to completion in no more than about 3 mins. at room temperature, more preferably in less than about 1 min., and most preferably in less than about 30 sec. It is believed that the reaction between gold salt and TAAC may occur at reasonable conversion substantially instantaneously at room temperature. Depending on stirring, temperature, and other conditions, however, other periods of time may be useful to carry out a method of the invention. Time periods of up to about 10 mins., for example, may be useful to insure maximum conversion. Some temperature elevation above room temperature may be useful to insure maximum conversion and reaction speed, although high temperatures are not necessary. By way of example, in addition to room temperature (approx. 25° C.), example methods of the invention may also be practiced at elevated temperatures of between about 35°-40° C., or between about 30°-35° C., or between about 25°-30° C.

The relatively high rates of conversion of gold salt to gold nanoparticles enjoyed by methods of the invention represent another important benefit of the present invention. Conversion to nanoparticles of at least about 70% of the gold contained in the gold salt, for example, may be achieved in the above described time periods (i.e., less than about 3 mins., preferably less than about 1 min, and more preferably less than about 30 sec) depending on conditions that include concentrations of reactants present, temperature, stirring, and the like. Higher conversions are also possible in methods of the invention, with at least about 90% conversion or at least about 98% more preferred in these time periods. It will be appreciated that the practice of the present invention at relatively low temperatures and high conversion rates offers important advantages and benefits over the prior art.

Still another valuable advantage of methods of the invention is that the size distribution of resultant gold nanoparticle can be at least partially tuned. In one example method of the invention, size of resultant gold nanoparticles is tuned through selection of stabilizer. Different stabilizers useful for practice of methods of the invention and resultant particle size ranges (expressed in diameter) that are believed to result from use of the stabilizer include:

Starch stabilized: about 18-22 nm, mean about 20 nm
Agarose stabilized: about 11-15 nm, mean about 13 nm
Glucose stabilized: about 20-24 nm, mean about 22 nm
Gum Arabic stabilized: about 8-12 nm, mean about 10 nm It is noted that with all of these stabilizers, relatively narrow size distributions are achieved. By way of example, at least about 80% of the gold nanoparticles produced through a method of the invention may have a uniform size range in the corresponding ranges listed above (e.g., at least about 80% in any of 18-22 nm, 11-15 nm, 20-24 nm, or 8-12 nm). It is further noted that all of these different stabilizers resulted in gold nanoparticle mean diameters (10 nm -22 nm) that are well suited for applications including biomedical ones. Other sizes are contemplated and can be achieved through selection of alternate stabilizers, reducing agent and ratio, with additional example sizes being between about 3-30 nm and others.

The distribution of nanoparticle sizes may also be at least partially tuned by varying the concentration of phosphino amino acid present. Taking TAAC as an example phosphino amino acid, it includes molecular cavities of about 5 nm in size. It is believed that gold nanoparticles are formed either on the surface of the TAAC or in its cavities. Particles formed on the surface will tend to have a larger size than those formed in the 5 nm cavities. To increase the number of small sized gold nanoparticles, the amount of TAAC present is increased to provide more cavities. To increase the number of large particle size gold nanoparticles, the amount of TAAC may be decreased, with more gold nanoparticles then being formed on the TAAC surface.

In addition to tuning particle size, an important purpose of stabilizers is to prevent agglomeration and/or oxidation of the gold nanoparticles during storage. All of the stabilizers identified above have been discovered to provide beneficial stability for gold nanoparticles produced through methods of the invention. TAAC, for instance, has been found to help "protect" gold nanoparticles from oxidation. Carbohydrates are an additional stabilizer discovered to be useful with practice of methods of the invention. More than one stabilizer may be employed. Any selected stabilizer can be added at any time during the synthesis of the nanoparticles. Preferably, the stabilizer is present in solution prior to introduction of the final reactant (i.e., one or both of gold salt and phosphino amino acid are added to a solution that already contains a stabilizer).

The stability in solution of gold nanoparticles, in addition to their retaining robust photophysical properties over a wide range of labeling and testing conditions, are important prerequisites for biomedical imaging or therapy applications. The stability of gold nanoparticles made and stabilized through methods of the invention has been found to be suitable for these and similar applications. Gold nanoparticles made using gold salt and TAAC were found to have a slightly tighter size distribution when stabilized with glucose than when stabilized with starch, although both were found to be suitable for biomedical applications.

In biomedical and similar applications, it is also desirable that dilution of gold nanoparticle solutions not alter their characteristic chemical and photophysical properties. Dilution has the potential of affecting the stability of gold nanoparticles. Dilution effects on gold nanoparticles made through methods of the invention using TAAC have been investigated. It has been discovered that stability of gold nanoparticles produced through methods of the invention did not change at dilutions in the range of 10M, 6M, and 8M (moles of gold per liter of solvent). These are typical concentrations encountered when working at cellular levels.

Another issue important to many gold nanoparticle applications, including in vivo imaging applications, is the stability of gold nanoparticles over a reasonable time period. The stability of gold nanoparticles produced through methods of the invention using TAAC was studied over a 7 day period. The gold nanoparticles stabilized with starch were discovered to experience appreciable agglomeration. In contrast, gold nanoparticles stabilized with glucose remained substantially stable and showed no appreciable agglomeration over a 7 day period. This suggests that glucose may be preferred over starch.

An additional method of the invention includes a step of using agarose as a stabilizer. Agarose is a polysaccharide containing agarobiose monomer. It is known to form a gel matrix that mimics the mechanical properties of biological tissue. As a result, the interaction of gold nanoparticles with an agarose matrix is considered to be a good model for understanding the interactions of gold nanoparticles with tumor tissue. Gold nanoparticles were produced through a method of the invention by reducing $NaAuCl_4$ with TAAC in the presence of hot (about 60-75° C.) 0.1% agarose solution in an aqueous media. Study of the gold nanoparticles indicated some agglomeration over a 7 day period of time, although less agglomeration occurred than in similarly produced gold nanoparticles when stabilized by starch. This slower rate of agglomeration may be attributed to trapping of gold nanoparticles in the pores within the agarose matrix.

It has been discovered that through methods of the invention gold nanochains and nanoarrays may be produced through addition of a chain forming agent. As used herein, the terms "nanoparticle chain" and/or "nanochain" are intended to be broadly interpreted as being a linked arrangement of at least 5 nanoparticles, and the term "nanoarry" is intended to refer to a subset of nanochains. A nanoarray generally includes nanoparticles linked in other than a linear shape to create some two or three dimensional linked shape. Nanochains may be linked together through electron sharing, and are characterized as being flexible along their length. Nanochains are not limited to a linear configuration, but also may adopt other linked configurations. By way of example, a ring or other clustering may be formed.

The chain forming agent may have the dual role of being a stabilizer. Preferably, the chain forming agent is provided after formation of the gold nanoparticles. One example chain forming agent includes void spaces such as surface pores or cavities that promote formation of chains by holding gold nanoparticles in close proximity to one another. Pores that accommodate at least about 5 nanoparticles in close proximity to one another, for instance, have been discovered to foster the formation of nanochains. It is, believed that as the particles are contained closely proximate to one another in the pores electron sharing bonds develop.

A preferred chain forming agent includes gum arabics, with agarose being one example. Agarose is useful to produce nanoarrays. Gum arabics are environmentally and biologically benign, and are generally available as a commodity item. Gum arabics have been discovered to include surface pores, cavities, and/or other void spaces that promote formation of gold nanochains. One example gum arabic that has proven useful in methods for forming gold nanochains is glycoprotein. It is believed that other proteins include void spaces that are beneficial for forming chains and will accordingly also be useful chain forming agents in methods of the invention.

In one example method for forming nanochains or arrays, it is desirable to arrange nanoparticles inside nanochannels. Such arrangement of imageable gold nanoparticles may provide models for their use in in-vivo applications (for example, in X-ray computer tomography (CT) imaging). Agarose is a mixture of complex carbohydrates and is well known as a gel material. The gel formation by agarose is mediated by complicated hydrogen bonds within the sugar moieties. Interpenetrating hydrogen bonds between sugar moieties form narrow channels, many of which are between about 100 to about 300 nanometers. The diameter of the nanochannel can be increased or decreased by engineering to a desired width, with one example step being use of a focused laser beam. An example width is of the order of microns (i.e., microchannels). The laser beam rearranges the hydrogen bonding structure within the sugar molecules to widen the nanochannels to microchannels.

One example method of the invention for forming nanochains involves direct filling of nanoparticles into nano channels, thus allowing nanoparticles to occupy spaces inside the channel and also fill the cavities. In terms of sequence, this example method includes first forming nanoparticles and then exposing the nanoparticles to a chain forming agent. This may include, for example, forming the nanoparticles in a container in an aqueous media and then introducing an agarose gel to the container. The particles enter the nanochannels of the gel as the aqueous media flows therein. If the nanoparticles are not anchored strongly to the cavities in the gel, they may leach out from the nanochannels through reverse osmosis. This method embodiment is referred to herein as "Method A."

Another example method of the invention for forming nanochains involves generating nanoparticles inside the cavity. In this embodiment, nanochannels are immersed inside an aqueous solution of gold salts (precursor material for gold nanoparticles), facilitating filling of cavities inside the channels with metal ions. At this stage, a nanoparticle initiator is allowed to flow through the channels. This nanoparticle initiator interacts with the precursor gold material, reduces the metal ion from +3 oxidation state to 0/+1 and initiates the formation of nanoparticles. This method embodiment is referred to herein as "Method B."

The size of the nanoparticles is to some extent dictated by the cavity size. In an additional step of some embodiments of Methods A and B of the invention, additional steps of removing nanoparticles not bound to the cavities and unreacted nanoparticle initiator molecules from the channels by washing with water or other suitable solvent. Nanoparticles bound to the cavities are permanently attached and are not easily removed by washings. Steps of washing can therefore be useful to further control resultant particle size. Cavities inside the channels are closely placed and allow nanoparticles to interact with each other to form nanochains or nanoarrays.

It has been discovered that both Methods A and B are useful to produce nanoarrays. Nanoarrays fabricated using Method A may "weep" out nanoparticles by suspension of the gel in water. In contrast, nanoarrays made using Method B appear to be very stable and do not appear to "weep" out nanoparticles, even after suspending the gel in water for prolonged periods of up to 15 days.

An example experimental procedure of Method B for the synthesis of a gold nanoarray involves the addition of $NaAuCl_4$ to agarose gel in water. After two minutes the reducing agent (TAAC) was added and stirred for an additional minute. Nanoarrays formed through this example method have been confirmed by Transmission Electron Microscopy (TEM) and Atomic Force Microscopy (AFM) images. Many overlapping arrays have been discovered to be produced through this method when examined using a TEM, which is expected as agarose gel will generally not produce coats of monolayers on the copper TEM grid. AFM study shows a long columnar formation of agarose-gel. Measurements indicate that the arrays formed have a length of up to about 270 nm and that the nanoparticles inside the nanochannels are of diameter of about 13 nm.

The stability of nanoparticles inside the nanoarray has also been studied to further characterize methods of the invention. For example, the surface activity of nanoparticles inside the nanoarray has been studied by direct interaction with cysteine. Cysteine molecules enter into the nanochannels and interact with nanoparticles inside. The results of these studies demonstrate that gold nanoarrays can be readily produced using biologically benign substrates.

Because chain forming agents such as gum arabics are environmentally and biologically benign, nanochains may be formed in-vivo, with examples including in mammals such as humans. This may be useful for medical and surgical applications, for example. Nanoarrays made through methods of the invention will be beneficial in applications, including, for example, as pre-fabricated gold nanoparticle probes for implantation in vivo for subsequent applications in X-ray contrast CT imaging and in ultra sound imaging. Methods for making nanoarrays of the invention result in effective localization of high populations of gold nanoparticles, which will also be beneficial in potential diagnostic and therapeutic applications where X-ray irradiation shrinks (or eliminates) specific tumors because of the selective absorption of high energy radiation by metallic nanoparticles and accordingly spares healthy tissue.

To further accommodate use of gold nanoparticles of the invention in some medical applications and similar applications, example methods of the invention include additional steps to further enhance the nanoparticles. These steps may include, for example, functionalizing the gold nanoparticles with one or more biomolecules. The term "biomolecule" as used herein is intended to be broadly interpreted, and may include a molecule from or derived from the biological sciences. Particular examples include but are not limited to peptides, proteins, antibodies, and biologically benign organic compounds. The term "functionalize" as used herein is also intended to be broadly interpreted, and may include for example to attach. One particular example step useful in different methods of the invention is to conjugate the gold nanoparticles with a biologically benign peptide or with a biologically benign protein.

Further example steps of functionalizing with a biomolecule are provided as follows:

Synthesis of Hybrid Gold Nanoparticles via Conjugation with Cysteine

Example applications for gold nanoparticles made through methods of the invention include use with tumors to detect, image, and to aid in reducing them. An important parameter concerning the suitability of gold nanoparticles for targeting tumor cells is the efficacy with which gold nanoparticles can be functionalized with hybrid biomolecules. Within methods of the invention, achieving target specificity of gold nanoparticles may be accomplished through steps of their conjugation with tumor-avid peptides or other biomolecules. It is desirable to develop conjugation protocols that do not adversely affect the receptor binding affinities of biomolecules. Steps of conjugating gold nanoparticles at about 25° C. and at physiological pH are well suited for the retention of binding affinity of target specific peptides used in labeling protocols with gold nanoparticles. As used herein, the term "labeling" is intended to be broadly interpreted, and may include attachment or conjugation.

Because gold nanoparticles have high reactivity with sulfhydryl (SH) groups, example methods of the invention utilize a biomolecule having a sulfhydryl group. Cysteine is a preferred example of a biomolecule useful to optimize gold nanoparticle labeling protocols. Efficient labeling of gold nanoparticles onto cysteine allows for translation of similar labeling protocols onto SH functionalized target specific peptides for the design and development of tumor specific gold nanoparticle-based imaging/therapeutic agents. Labeling of gold nanoparticles onto cysteine is also beneficial because this is a common thiolated amino acid present in several biologically relevant proteins and synthetic peptides.

A step of determining the amount of cysteine needed to conjugate and saturate the gold nanoparticles may be performed. One example step for doing so exploits the condition that nanoparticles that are not conjugated with a strong ligand such as cysteine will agglomerate upon addition of NaCl. Accordingly, the number of gold nanoparticles not conjugated with cysteine determines the degree of aggregation produced when NaCl is added to the nanoparticles. The degree of aggregation can be measured using any of several suitable methods well known in the art, including TEM. At low cysteine concentrations, few gold nanoparticles are conjugated with cysteine, therefore aggregation is observed upon addition of NaCl. At optimal cysteine concentrations, on the other hand, all gold nanoparticle sites are saturated with cysteine. At this end point in the gold nanoparticle-cysteine titration, further addition of NaCl causes no significant aggregation. The average size of the gold nanoparticle remains substantially unchanged under cysteine conjugation. These results suggest that cysteine conjugation of gold nanoparticles results in the retention of useful photophysical properties of gold nanoparticles. In vitro stability of cysteine conjugated gold nanoparticles revealed that these hybrid gold nanoparticles are stable for over two days.

Gold Nanochain Fabrication via Bioconjugation with Glycoproteins

Other steps of example methods of the invention include conjugating the gold nanoparticles with a biomolecule such as a protein to develop a viable gold nanoparticle labeling approach for potential applications such as labeling target specific biological proteins or peptides with gold nanoparticles. An example protein is a gum arabic, with arabino galactan (AG) being a preferred example. AG is a glyco protein extensively used in the food industry. It is a mixture of lower molecular weight polysaccharide (M.Wt. approx. $0.25 \times 10^6$; major component) and higher molecular weight hydroxyproline-rich glycoprotein (M.Wt. about $2.5 \times 10^6$ minor component). An example embodiment of the invention includes labeling arabino galactan (AG) protein with gold nanoparticles simultaneously as the nanoparticles are produced.

Example steps include reducing a gold salt such as $NaAuCl_4$ with a phosphino amino acid such as TAAC in the presence of AG in an aqueous media. The gold nanoparticles thus formed are labeled with AG. Absorption measurements indicate that the plasmon resonance wavelength and plasmon line width of resultant AG conjugated gold nanoparticles (AG-gold nanoparticles) are about 540 nm and about 151 nm respectively. The size of the AG-gold nanoparticles is found to be about 10 nm. The stability of the AG-gold nanoparticles was evaluated by monitoring the plasmon resonance wavelength and plasmon band width over a 28 day period.

During the initial 4 days, some indication of nanochain formation is found. Formation of nanochains is found to be approximately linear with time. Interestingly, after 20 days, significant formation of nanochains is indicated. Furthermore, TEM images of fresh and 20 day old AG-Gold nanoparticles reveal the formation of long chain like structures due to amalgamation of AG-Gold nanoparticles. The nanochain formed enables delivery of more nanoparticles with a single AG molecule—a result of considerable value for potential imaging, therapeutic and other applications. The gold nanochain formation may provide new avenues for maximizing the concentration of gold nanoparticles on tumor cells/ tumor tissue, thus increasing the diagnostic/therapeutic dose of gold nanoparticles.

Hybrid Gold Nanoparticles Functionalized with Tumor Specific Peptides

Through example methods of the invention, gold nanoparticles can be directed to tumor sites for potential applications in the development of cancer diagnostic/therapeutic agents. One example objective is to utilize contrast enhancements of gold nanoparticles in X-ray Computer Tomography (CT) and ultrasound (US) imaging techniques. Therapeutic analogs of gold nanoparticles can be produced using the corresponding emitting Au-198 isotope within methods of the invention. Example methods of the invention can include steps of conjugating gold nanoparticles with a peptide. Steps of conjugating to link gold nanoparticles with a tumor-avid peptide can be beneficial and advantageous for the design and development of cancer specific diagnostic and therapeutic agents.

Conjugation protocols for labeling nanoparticles of gold and other metals with tumor specific peptides have been developed. An example method of the invention contemplates exploiting bombesin peptide, although many other peptides will be suitable for use in methods of the invention. The 14-amino acid peptide bombesin (BBN) isolated from the skin of the amphibian Bombina and related gastrin-releasing peptides (GRP) exhibit an enhanced response in a variety of tumor tissues, e.g., in small cell lung, prostate, breast, and colon cancer. Analogues of bombesin with modified structures exhibited a similar or even higher affinity for these receptors. Synthetic peptides can be readily generated through automated solid phase techniques. Within example methods of the invention, the seven-amino acid truncated bombesin analogue (BBN) has been produced and utilized as a vehicle to target GRP receptors. The peptide BBN has been shown in the literature to be a potent GRP agonist. It can be radiolabeled with 123/131I, 99 mTc or 105 Rh for potential nuclear medical applications by virtue of its retention of a high binding affinity for GRP receptors.

It is contemplated that additional steps of an example method of the invention will include introduction of additional spacer functions (for example, in the form of 5-aminopentanoic acid) to the N-terminal region of the peptide to avoid interference of the chelating moiety with the receptor binding C-terminus of the peptide. These steps are believed to maximize binding of gold nanoparticle labeled peptide with receptors over expressed on prostate cancer cells. Bombesin attached to 5 carbon linker was synthesized by standard solid phase peptide synthesis techniques. Thioctic acid conjugated bombesin (SS—NH-5C—BBN) was synthesized by conventional activation of the carboxylate group by HBTU followed by treatment with NH2-5C—BBN. Formation of SS—NH-5C-BBN was established from mass spectral data. The SS-NH-5C—BBN was conjugated to gold nanoparticles (20 nm) to produce hybrid nanoparticle gold nanoparticle-SS—NH-5C—BBN. The formation of hybrid nanoparticle gold nanoparticle-BBN conjugates was confirmed by UV-Vis spectroscopy, TEM and MS analysis.

Synthesis of Radioactive Gold Nanoparticles

Other example methods of the invention include production of radioactive gold nanoparticles. Also, in some applications such as medical treatment and the like, a radioactive gold nanoparticle may prove useful. Radioactive gold containing materials may be used in methods of the invention as described above to produce radioactive gold nanoparticles. For example, reacting a gold salt with a phosphino amino, with a preferred example being the trimeric phosphino amino acid TAAC (P(CH$_2$NHCH(CH$_3$)COOH)$_3$) results in the formation of nanoparticulate gold. A well defined particulate size, with an example being 15-20 nm, can be obtained. A general reaction scheme for a preferred reaction is:

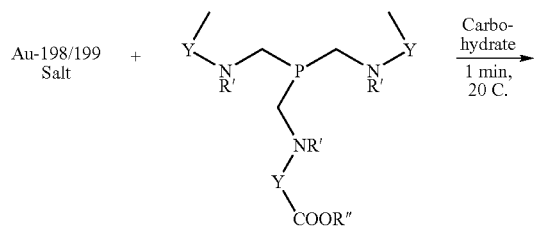

-continued

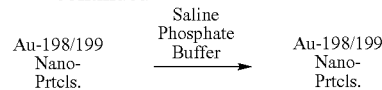

This and similar methods for producing radioactive gold nanoparticles are particularly useful for medical and bio-applications due to the nontoxic nature of the nanoparticle initiator TAAC and because the gold nanoparticle formation by this method proceeds in aqueous media. Other benefits are achieved since the reaction is efficient for the production of radioactive nanoparticulate gold even at concentrations of 10-12 M.

In one example procedure, MURR irradiation facilities were used for the production of Au-198/Au-199. Gold foil (5-30 mg) was irradiated at a flux of about $8\times10^{13}$ n/cm$^2$/s. The radioactive foil was dissolved with aqua regia, dried down and reconstituted in 0.5-1 mL of 0.05 N HCl to form HAuCl$_4$. The radioactive gold (50-100 µL) solution was added to aqueous solutions (6 mL) containing starch or other stabilizers such as glucose or arabinogalactan, followed by a solution containing TAAC (20 µL) for initiating to form radioactive nanoparticles according to the above preferred reaction. A saline phosphate buffer solution was added to adjust the pH. Other buffer solutions are appropriate for use. Other steps of other example methods of the invention may also be practiced, including, for example addition of a chain forming agent such as a gum arabic.

The addition of TAAC resulted in a color change from yellow to a burgundy purple. This color change is diagnostic of plasmon-plasmon transition present in nanoparticulate gold. This plasmon transition at the tracer level for Au-198/Au-199nanoparticle was further confirmed by measurement using a UV- Visible spectrophotometer.

Gold Nanopartiele Stabilization/Storage

Still additional example methods of the invention are directed to methods for storing and/or stabilizing gold nanoparticles. It has been discovered the use of phosphino amino acids, with TAAC being a preferred example, provide beneficial levels of stability for storing gold nanoparticles. In an example method of the invention, gold nanoparticles (that may have been, for example, produced through a method other than one of the present invention) are exposed to a phosphino amino acid such as TAAC to prevent their agglomeration. It has been discovered that these example steps can be useful to substantially prevent agglomeration over periods of 7, 14 and even 30 days.

In Vivo Applications

It will be appreciated that methods of the invention thereby provide important and valuable benefits over the prior art. For example, because gold nanoparticles can be produced at room temperature, at physiologic pH, at high conversion rates and with biologically benign reactants that are not toxic or hazardous, methods of the invention are particularly well suited to both in-vitro and in-vivo practice.

Gold nanoparticles may be made, for example, in a living organism such as a mammal. By way of example, it may be desirable to make use of the marking or tracing properties of gold nanoparticles for medicinal, research, or other purposes in a human being or an animal. In such cases, a gold salt could be dispersed in an area of interest (during a surgery on an organ, for instance), with a phosphino amino acid solution then introduced to the area, through dropwise addition or spraying, for example. Gold nanoparticles would result. Further, it may be practical to rely on the phosphino amino acids present in proteins to produce gold nanoparticles by introducing a gold salt. If gold nanochains were desired, a biologically benign chain forming agent could likewise be added, with an example being a gum arabic such as glycoprotein. Likewise, a patient might ingest one or both of the reactants (and a chain forming agent) so that gold nanoparticles would be produced in the mouth, throat, stomach, or digestive tract as desired.

Other applications in which methods of the invention may find utility is military or commercial applications in which it is desired to produce gold nanoparticles and/or nanochains quickly, on-site in the field and through a simple procedure for purposes including imaging, tagging, and the like. A soldier in combat or a field service technician, for instance, could potentially tear open a two-compartment foil packet with a small amount of a gold salt solution in one compartment and a small amount of TAAC in the second. Combining the two materials in an area of interest would produce gold nanoparticles there for later tracking or detection. A third compartment might include a chain forming agent that could likewise be added.

Other embodiments of the invention, in fact, are directed to articles that contain reactants useful to practice methods of the invention. One example article of the invention has at least a first and a second compartment. Each compartment contains a material useful to practice a method of the invention as discussed herein above that are useful to practice methods of the invention. For example, the first compartment may contain a gold containing material such as a gold salt and a second may contain a phosphino amino acid such as TAAC. Third and additional compartments may be provided, which may include a chain forming agent, stabilzers, or other materials. Alternatively, chain forming agent(s) and/or stabilizers may be present in the second compartment in a two compartment article. A solvent, stabilizer, and other materials may be provided in one or more of the compartments. The compartments should be substantially sealed to prevent potentially contaminating exposure to air or liquid. The article is preferably small and portable, with examples articles including a small foil or polymer article that is disposable.

FIG. 1 schematically shows one example article of the invention. The article 10 is a two sided substantially flat packet. The two sides of the packet are defined by thin flat sheets of foil, polymer, or other material that is substantially impervious to gas and liquid. The sheets may be sealed about their edges or elsewhere to define the two compartments between them. One of the sides 12 is shown in FIG. 1, with the two compartments 14 defined by the sealed regions of the sides 12 that surround them. Such an article could be configured for easy opening by tearing or cutting, and may include, for example, a perforation or otherwise weakened section 16 for ease of tearing. Each compartment 14 and 16 might contain only a few milli or even micro grams of reactants. The packet 10 might be very small in size, with an example being less than two square inches. A user could open the compartments 12 and 14 by tearing or cutting them along the line 18 and combine the reactants in a desired location. Example applications for use of articles of the invention such as the packet 10 include medical application by surgeons or others who would open the compartments 12 and 14 during a medical procedure such as a surgery and deposit the contents in a desired location in a patient to form gold nanoparticles there. Another example article of the invention is one that is ingestible by a patient and that dissolves internally to release the reactants. One example is a capsule having separate compartments.

While specific embodiments of the present invention have been shown and described, it should be understood that other modifications, substitutions and alternatives will be apparent to those knowledgeable in the field involved. For example, while methods of the invention have been described using a particular sequence of steps, it will be appreciated that unless specifically appreciated that as used herein the term "acid" encompasses corresponding salts. Such modifications, substitutions and alternatives can be made without departing from the spirit and scope of the invention as set forth in the following claims.

The invention claimed is:

1. A method for producing gold nanoparticles comprising the steps of:
   providing a gold salt;
   providing a phosphino amino acid including three alanines bound across an alkyl chain to a phosphorous center;
   reacting said gold salt with said phosphino amino acid to make gold nanoparticles that are non-toxic, biologically benign and suitable for use in biologic applications.

2. The method of claim 1 wherein said phosphino amino acid is one or more of a tris(N-methylaminoacid) phosphine or a bis(N,N-dimethylaminoacid) phosphine, and wherein said gold salt includes ionic gold that may be reduced.

3. The method of claim 1 wherein said phosphino amino acid is 2, 2', 2"-(phosphineyltris(methylene))tris(azanediyl) tripropanoic acid.

4. The method of claim 1 wherein said phosphino amino acid comprises:

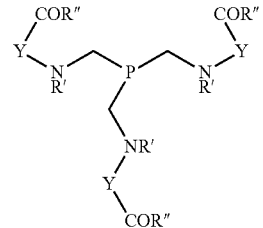

where:
R'=hydrogen,
R"=OR$^4$ where R$^4$=hydrogen, and
Y=CH(R) where R is methyl.

5. The method of claim 1 wherein said gold salt includes gold in a plus 3 ionic state, and wherein the step of reacting said gold salt with said phosphino amino acid to make gold nanoparticles is performed at a temperature of less than about 30° C. and converts at least about 70% of the gold in said gold salt to gold nanoparticles in a time period of less than about 1 min.

6. The method of claim 1 wherein the step of reacting said gold salt with said phosphino amino acid results in gold nanoparticles having a spherical shape with at least about 80% of which have a diameter between about 10 and about 22 nm.

7. The method of claim 1 wherein the step of reacting said gold containing material with said phosphino amino acid occurs at physiological pH and wherein the resultant nanoparticles have a diameter of between about 8 to about 22 nm that remain substantially free from agglomeration.

8. The method of claim 1 and further including the step of forming gold nanochains by exposing said gold nanoparticles to a gum arabic.

9. The method of claim 1 wherein the method is further for making a nanochain of gold nanoparticles, and further includes the step of exposing said gold nanoparticles to a nanochain forming agent having void spaces in which said gold nanoparticles are held in close proximity to one another.

10. The method of claim 9 wherein said nanochain forming agent is agarose, and wherein said nanochains comprise nanoarrays.

11. The method of claim 1 and further including the step of providing a chain forming agent having nanochannels, wherein the step of providing a gold salt includes introducing said gold salt into said nanochannels, and wherein the step of providing said phosphino amino acid includes introducing said phosphino amino acid into said nanochannels with said gold salt present in said nanochannels, and further including the step of washing said nanochannels with a solvent.

12. The method of claim 1 and further including the step of exposing said gold nanoparticles to one or more stabilizers selected from the group of stabilizers consisting essentially of: starch, agarose and glucose; and,
storing said gold nanoparticles for a period of at least about 2 weeks without substantial agglomeration of said nanoparticles.

13. The method of claim 1 wherein the method is carried out within a mammal.

14. The method of claim 13 wherein said mammal is a human being, and wherein the step of reacting a gold salt with a phosphino amino acid further includes introducing said gold salt and said phosphino amino acid to a selected area of said human being to produce said gold nanoparticles in said selected area.

15. The method of claim 1 and further including the step of functionalizing said gold nanoparticles with a biomolecule selected from the group consisting of peptides, proteins and compounds having a sulfhydryl group.

16. The method of claim 1 and further including the step of functionalizing said gold nanoparticles with a biomolecule by conjugating said gold nanoparticles at about 25° C. and at physiological pH with said biomolecule, and wherein said biomolecule comprises at least one of a peptide, a protein and a biomolecule having a sulfhydryl group.

17. The method of claim 1 wherein said gold salt includes radioactive gold isotopes, and wherein said gold nanoparticles are radioactive.

18. A method for forming gold nanochains comprising the steps of:
reacting a gold salt with a phosphino amino acid that comprises three alanines bound across an alkyl chain to a phosphorous center to form gold nanoparticles are non-toxic, biologically benign and suitable for use in biologic applications; and,
exposing said gold nanoparticles to a chain forming agent having a plurality of cavities in close proximity to one another and operable to hold gold nanoparticles in close proximity to one another wherein nanochains of gold are formed.

19. A method for forming gold nanochains as defined by claim 18 wherein said nanochains comprise nanoarrays, and wherein said chain forming agent comprises agarose.

20. An article for forming gold nanoparticles comprising:
a first sealed compartment containing a gold salt;
a second sealed compartment isolated from said first and containing a phosphino amino acid; and,
wherein said first and second compartments are configured to be opened wherein said gold salt and said phosphino amino acid may be combined to form gold nanoparticles.

21. An article for forming gold nanoparticles as defined by claim 20 wherein said article comprises two substantially flat sheets sealed to one another to define said first and second compartments therebetween.

22. A method as defined by claim 1 wherein the resulting gold nanoparticles are not bound to phosphine oxide.

23. A method as defined by claim 1 wherein:
the phosphine amino acid is oxidized during the reaction to yield a corresponding phosphine oxide which is further consumed to assist the conversion of gold nanoparticles;
the reduction of the gold salt is initiated by phosphino amino acid; and, and,
aminocarboxylates in the phosphine oxide serve as a reducing agent to reduce the gold salt to gold nanoparticles.

* * * * *

UNITED STATES PATENT AND TRADEMARK OFFICE
CERTIFICATE OF CORRECTION

| | |
|---|---|
| PATENT NO. | : 8,241,393 B2 |
| APPLICATION NO. | : 11/219497 |
| DATED | : August 14, 2012 |
| INVENTOR(S) | : Ragharaman et al. |

It is certified that error appears in the above-identified patent and that said Letters Patent is hereby corrected as shown below:

In the Specification:
Col. 7, line 11        Please delete "nanoarry" and insert --nanoarray-- therefor.
Col. 13, line 30       Please delete "stabilzers" and insert --stabilizers-- therefor.

In the Claims:
Claim 23, Col. 16, line 35    Please delete the second occurrence of "and,".

Signed and Sealed this
Twenty-eighth Day of May, 2013

Teresa Stanek Rea
*Acting Director of the United States Patent and Trademark Office*